US011253406B2

(12) United States Patent
Kuwahata (10) Patent No.: US 11,253,406 B2
(45) Date of Patent: Feb. 22, 2022

(54) ABSORBENT ARTICLE AND METHOD FOR MANUFACTURING SHEET WITH THREE-DIMENSIONAL OPENING USED THEREFOR

(71) Applicant: Kao Corporation, Tokyo (JP)

(72) Inventor: Kohei Kuwahata, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 395 days.

(21) Appl. No.: 16/338,959

(22) PCT Filed: Oct. 16, 2017

(86) PCT No.: PCT/JP2017/037357
§ 371 (c)(1),
(2) Date: Apr. 2, 2019

(87) PCT Pub. No.: WO2018/100901
PCT Pub. Date: Jun. 7, 2018

(65) Prior Publication Data
US 2021/0205153 A1 Jul. 8, 2021

(30) Foreign Application Priority Data
Nov. 30, 2016 (JP) .............................. JP2016-233181

(51) Int. Cl.
*A61F 13/511* (2006.01)
*A61F 13/512* (2006.01)

(52) U.S. Cl.
CPC ...... *A61F 13/5125* (2013.01); *A61F 13/5116* (2013.01); *A61F 13/51104* (2013.01); *A61F 2013/51178* (2013.01)

(58) Field of Classification Search
CPC ............ A61F 13/51104; A61F 13/5116; A61F 13/512; A61F 13/5121; A61F 13/5123;
(Continued)

(56) References Cited

U.S. PATENT DOCUMENTS 5,188,625 A * 2/1993 Van Iten ........... A61F 13/15577
604/383
8,030,536 B2 * 10/2011 Ponomarenko ....... A61F 13/512
604/383
(Continued)

FOREIGN PATENT DOCUMENTS

CN 1177027 A 3/1998
CN 1496728 A 5/2004
(Continued)

OTHER PUBLICATIONS

International Search Report for PCT/JP2017/037357 (PCT/ISA/210) dated Dec. 19, 2017.

*Primary Examiner* — Catharine L Anderson
(74) *Attorney, Agent, or Firm* — Birch, Stewart, Kolasch & Birch, LLP (57) ABSTRACT

A topsheet (2) includes a laminate of a first nonwoven fabric (20) and a second nonwoven fabric (21), the two nonwoven fabrics (20, 21) are fused together at peripheral edges of openings (22) to form a plurality of fusion bond portions (23), and the first nonwoven fabric (20) in a region other than the fusion bond portions (23) protrudes in a direction away from the second nonwoven fabric (21) to form a plurality of projections (24) protruding toward the skin of a wearer. Each fusion bond portion (23) has a protrusion (26) protruding toward a sublayer (3), and a plurality of the protrusions (26) are dispersed on a surface (2b) of the topsheet (2) facing the sublayer (3). When the topsheet (2) is pressed toward the sublayer (3), the sublayer (3) is partially pressed by the protrusions (26).

19 Claims, 5 Drawing Sheets (58) Field of Classification Search
CPC .............. A61F 13/5125; A61F 13/5126; A61F 2013/51182; A61F 2013/51338; A61F 2013/51344
See application file for complete search history.

(56) References Cited

U.S. PATENT DOCUMENTS

| | | | |
|---|---|---|---|
| 8,182,728 B2* | 5/2012 | Cree | A61F 13/537 264/156 |
| 10,821,036 B2* | 11/2020 | Xie | B32B 38/04 |
| 10,857,042 B2* | 12/2020 | Burger | B32B 3/266 |
| 10,912,682 B2* | 2/2021 | Takahashi | A61F 13/51104 |
| 2001/0008683 A1 | 7/2001 | Takai et al. | |
| 2001/0052381 A1 | 12/2001 | Takai et al. | |
| 2002/0022427 A1 | 2/2002 | Curro et al. | |
| 2021/0205154 A1* | 7/2021 | Kurihara | A61F 13/51113 |

FOREIGN PATENT DOCUMENTS

| | | |
|---|---|---|
| CN | 1642501 A | 7/2005 |
| CN | 1976660 A | 6/2007 |
| CN | 103619294 A | 3/2014 |
| CN | 204112013 U | 1/2015 |
| EP | 2226046 A1 | 9/2010 |
| JP | H04-152945 A | 5/1992 |
| JP | 2002-345883 A | 12/2002 |
| JP | 2004-275296 A | 10/2004 |
| JP | 2006-255051 A | 9/2006 |
| JP | 2009-039177 A | 2/2009 |
| JP | 2013-111169 A | 6/2013 |
| JP | 2015-142721 A | 8/2015 |
| TW | M528734 U | 9/2016 |
| WO | WO 2013/005782 A1 | 1/2013 |

\* cited by examiner

ABSORBENT ARTICLE AND METHOD FOR MANUFACTURING SHEET WITH THREE-DIMENSIONAL OPENING USED THEREFOR

TECHNICAL FIELD

The present invention relates to an absorbent article including a three-dimensional perforated sheet in which two nonwoven fabrics are partially fused and integrated.

BACKGROUND ART

Absorbent articles such as disposable diapers include a topsheet that is a member highly frequently coming into contact with the skin of a wearer, and thus properties including liquid permeability and good texture are highly valued. Hence, various techniques have been disclosed to improve such properties. For example, Patent Literature 1 discloses a topsheet having a single layer structure of a nonwoven fabric in which a plurality of liquid conduits are dispersed, and each liquid conduit protrudes toward the side opposite to the skin of a wearer (absorbent member side) and has a top opening and a bottom opening. On the skin-facing surface of the topsheet, a plurality of top openings of the liquid conduits are dispersed, and projections protruding toward the skin of a wearer are not formed. The opening peripheral edge of the bottom opening of each liquid conduit is so formed as to have a higher density than the other part of the liquid conduit or as to have a rib and is so provided as to be in contact with a skin-facing surface of an absorbent member that is provided on the non-skin-facing surface of the topsheet. It is therefore thought that even when an external force is applied to the liquid conduits due to, for example, body movement of a wearer wearing the absorbent article, the bottom openings are scarcely closed, and thus excrements can be quickly delivered through the liquid conduits to the absorbent member. However, in the topsheet according to Patent Literature 1, a three-dimensional portion of each liquid conduit between the top opening and the bottom opening is likely to collapse when a body pressure of a wearer is applied. Hence, even when the bottom openings are unlikely to be closed, the route of excrements to the bottom openings is likely to be closed, and thus the topsheet has insufficient liquid permeability.

Patent Literature 2 discloses a topsheet including a three-dimensional sheet in which a first nonwoven fabric and a second nonwoven fabric are partially fusion bonded to form fusion bond portions and the first nonwoven fabric in non-fusion bond portions surrounded by the fusion bond portions protrudes in the direction away from the second nonwoven fabric to form a large number of hollow projections. Inside each outline of the fusion bond portions of the topsheet, a through-hole having an outer peripheral edge with a similar shape to the shape of the outline is formed, and it is thought that the through-holes and the hollow projections enable reduction in remaining liquid on the skin-facing surface or in returning liquid to suppress redness and irritation of the skin of a wearer. The peripheral part of the outer peripheral edge of each through-hole is made into a film with no fiber shape of constituent fibers of the nonwoven fabric, and protrudes toward the center of the through-hole, but does not protrude in the thickness direction of the topsheet.

CITATION LIST

Patent Literatures

Patent Literature 1: JP 4-152945 A
Patent Literature 2: JP 2015-142721 A

SUMMARY OF INVENTION

The present invention relates to an absorbent article having a longitudinal direction coincident with a front-to-rear direction of a wearer and a lateral direction orthogonal to the longitudinal direction. The absorbent article includes a topsheet, a liquid-permeable sublayer, and a liquid-retentive absorbent member, and the topsheet, the liquid-permeable sublayer, and the liquid-retentive absorbent member are sequentially stacked in increasing order of distance from a skin of a wearer. The topsheet includes a laminate of a first nonwoven fabric and a second nonwoven fabric, and the laminate has a plurality of openings penetrating the laminate in a thickness direction. The first nonwoven fabric and the second nonwoven fabric are fused together at peripheral edges of the openings to form a plurality of fusion bond portions. The first nonwoven fabric in a region other than the fusion bond portions protrudes in a direction away from the second nonwoven fabric to form a plurality of projections protruding toward a skin of a wearer. Each fusion bond portion of the topsheet has a protrusion protruding toward the sublayer, and a plurality of the protrusions are dispersed on a surface of the topsheet facing the sublayer. When the topsheet is pressed toward the sublayer, the sublayer is partially pressed by the protrusions of the topsheet.

The present invention also relates to a method for manufacturing a three-dimensional perforated sheet that includes a laminate of a first nonwoven fabric and a second nonwoven fabric, the laminate has a plurality of openings penetrating the laminate in a thickness direction, the first nonwoven fabric and the second nonwoven fabric are fused together at peripheral edges of the openings to form a plurality of fusion bond portions, the first nonwoven fabric in a region other than the fusion bond portions forms a plurality of projections protruding in a direction away from the second nonwoven fabric, and each fusion bond portion has a protrusion protruding toward a side opposite to the projections. The method for manufacturing a three-dimensional perforated sheet of the present invention includes an unevenness forming step of using a first roller having a peripheral surface with an uneven shape and a second roller having a peripheral surface with an uneven shape that is to engage with the uneven shape of the first roller and allowing an engagement portion between the two rollers to bite the first nonwoven fabric to form unevenness on the first nonwoven fabric and a fusing and perforating step of, while the first nonwoven fabric with the formed unevenness is supported on the peripheral surface of the first roller, laminating the second nonwoven fabric on the first nonwoven fabric, fusing the second nonwoven fabric with the first nonwoven fabric at positions corresponding to projections of the first roller to form the fusion bond portions, and further forming the openings at forming positions of the fusion bond portions. In the fusing and perforating step includes bringing a tip of a projection of the first roller is into contact with the first nonwoven fabric at a position where the opening is to be formed, and concurrently, allowing the projection to penetrate a melted part, so that a meltage of the fusion bond portion is unevenly distributed on a side of the second nonwoven fabric, thereby forming the protrusion.

DESCRIPTION OF EMBODIMENTS

Excrements to be absorbed by absorbent articles include an excrement having a comparatively low viscosity, such as urine, and an excrement having a comparatively high viscosity, such as loose feces. For low viscosity excrements, capillary force is comparatively effective, and such excrements are likely to move to a portion having a high fiber density. In contrast, high viscosity excrements cannot penetrate a portion having a high fiber density. Hence, to quickly deliver the high viscosity excrements through a topsheet to an absorbent member, other improvements than those for low viscosity excrements are required. For example, such openings penetrating through a topsheet in the thickness direction as disclosed in Patent Literatures 1 and 2 are effective in improving the permeability for high viscosity excrements. Separately, a technique of interposing a liquid-permeable sheet called a sublayer or the like between a topsheet and an absorbent member has been known, and the technique is effective in improving the permeability for high viscosity excrements.

However, when a conventional topsheet including a high fiber density portion effective in improving the permeability for low viscosity excrements and openings effective in improving the permeability for high viscosity excrements is used in combination with a sublayer, such a density gradient that the outer side has a higher fiber density than the inner side is formed between the topsheet positioned at the outer side of an absorbent article in the thickness direction and the sublayer positioned at the inner side, and this reduces the permeability for low viscosity excrements including urine.

An absorbent article having excellent absorbability for both of low viscosity excrements and high viscosity excrements has not been developed yet.

The present invention relates to an absorbent article having excellent absorbability for both of low viscosity excrements and high viscosity excrements, and a method for manufacturing a three-dimensional perforated sheet used for the absorbent article.

Figure 1:
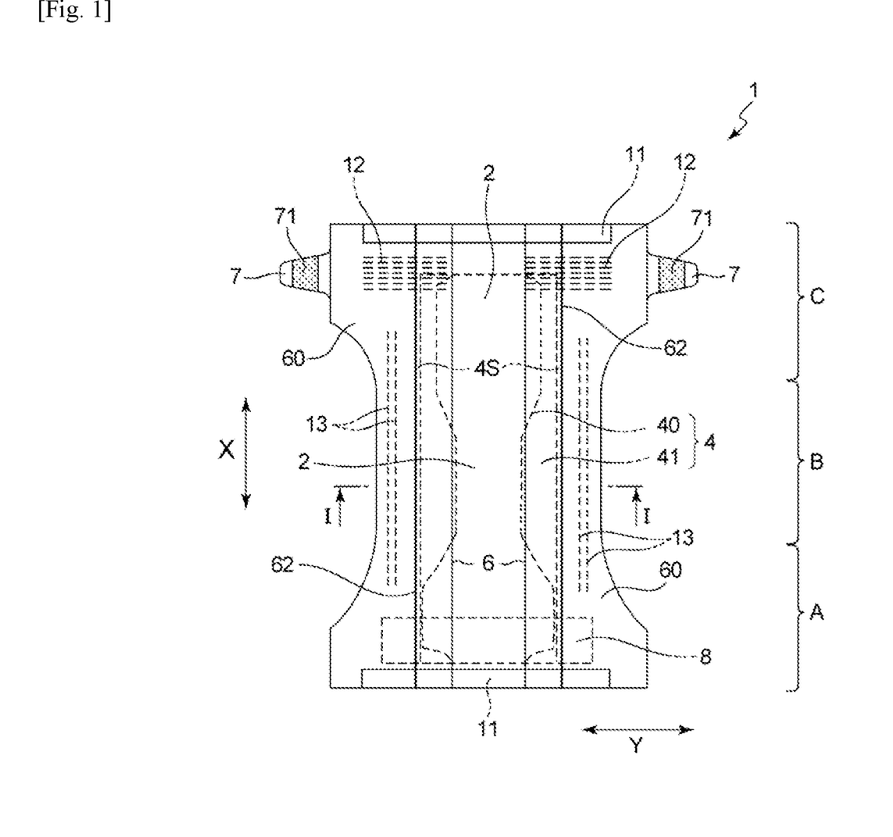
FIG. 1 is a schematic plan view showing a skin-facing surface, or a topsheet side, of an open type disposable diaper as an embodiment of an absorbent article of the present invention and is a plan view in which elastic members of each portion are stretched to spread the diaper into a plane.
Figure 2:
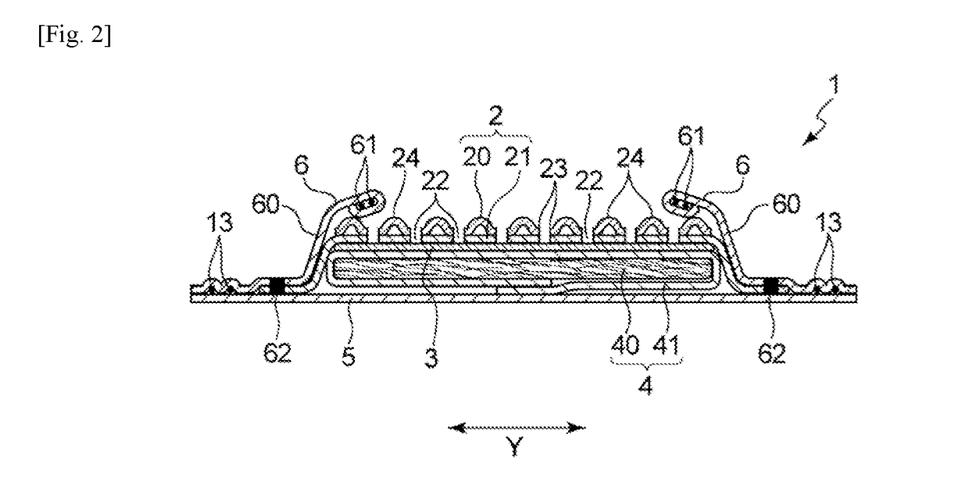
FIG. 2 is a schematic sectional view showing a cross section taken along line I-I in FIG. 1.

An absorbent article of the present invention will now be described on the basis of an open type disposable diaper as a preferred embodiment, with reference to drawings. FIG. 1 and FIG. 2 show an open type disposable diaper 1 of the embodiment. The diaper 1 has a longitudinal direction X coincident with the front-to-rear direction of a wearer and a lateral direction Y orthogonal to the longitudinal direction X, and includes a crotch portion B to be placed on the crotch of a wearer and a front portion A and a rear portion C extending forward and backward from the crotch portion B. The front portion A, the crotch portion B, and the rear portion C correspond to trisected regions of the diaper 1 in the longitudinal direction X. The crotch portion B has an excretory-facing region to face the excretory part including the penis and the anus of a wearer wearing the diaper 1, and the excretory-facing region is located at or around the center of the diaper 1 in the longitudinal direction X.

In the diaper 1, as shown in FIG. 2, a topsheet 2, a liquid-permeable sublayer 3, and a liquid-retentive absorbent member 4 are sequentially stacked in increasing order of distance from the skin of a wearer. More specifically, the diaper 1 includes an absorbent member 4, a topsheet 2 provided on a skin-facing surface side of the absorbent member 4 and overlying the absorbent member 4 at a position closer to the skin of a wearer than the absorbent member 4, a backsheet 5 provided on a non-skin-facing surface side of the absorbent member 4 and overlying the absorbent member 4 at a position more distant from the skin of a wearer than the absorbent member 4, and a sublayer 3 interposed between the topsheet 2 and the absorbent member 4. In such a plan view as shown in FIG. 1, the central part in the longitudinal direction X located in the crotch portion B is narrow and long in one direction, or in the longitudinal direction X, and forms a sandglass-like shape oblong in the longitudinal direction. Each of the topsheet 2 and the backsheet 5 has larger dimensions than those of the sublayer 3 and the absorbent member 4 that are interposed between the sheets 2, 5 and forms the outer shape of the diaper 1 in its flat-out, uncontracted state as shown in FIG. 1. As the backsheet 5, various sheets conventionally used in such absorbent articles can be used without any limitation. For example, a resin film or a laminate of a resin film and a nonwoven fabric can be used.

In the present specification, a "skin-facing surface" is one face of an absorbent article or a constituent member thereof (for example, a topsheet 2) and faces the skin of a wearer at the time of wearing of the absorbent article or is the face relatively close to the skin of a wearer, and a "non-skin-facing surface" is the other face of an absorbent article or a constituent member thereof and is the face opposite to the skin of a wearer at the time of wearing of the absorbent article (the side on clothes) or is the face relatively distant from the skin of a wearer. In the present specification, "at the time of wearing" means a condition in which a typical, appropriate wearing position is maintained, and excludes the case in which an absorbent article is displaced from an appropriate wearing position.

The sublayer 3 has functions including improvement of liquid permeability from the topsheet 2 to the absorbent member 4 and reduction of liquid returning of a liquid absorbed by the absorbent member 4 to the topsheet 2, and overlies substantially the whole region of the skin-facing surface of the absorbent member 4. In the present embodiment, the sublayer 3 has a single layer structure with a rectangular shape in a plan view, has substantially the same shape and dimensions in its plan view as those of the absorbent member 4, and does not extend outward from the periphery edge of the absorbent member 4. As the sublayer 3, a hydrophilic and liquid-permeable sheet can be used, and specific examples include paper, woven fabric, and nonwoven fabric. From the viewpoint of comparatively high strength and excellent flexibility, nonwoven fabric is more preferred. Examples of the nonwoven fabric constituting the sublayer 3 include an air-through nonwoven fabric, a point bond nonwoven fabric, a resin bonded nonwoven fabric, a spunlace nonwoven fabric, and an airlaid nonwoven fabric. Of them, an air-through nonwoven fabric, a resin bonded nonwoven fabric, and an airlaid nonwoven fabric easily absorb high viscosity excrements due to bulkiness and low fiber densities and thus are preferred. The sublayer 3 preferably has a basis weight of 10 g/m$^2$ or more, more preferably 15 g/m$^2$ or more, and preferably 100 g/m$^2$ or less, more preferably 70 g/m$^2$ or less.

The absorbent member 4 has a long shape in the longitudinal direction X in such a plan view as shown in FIG. 1 and extends from the front portion A to the rear portion C. The absorbent member 4 includes a liquid-retentive absorbent core 40 containing an absorbent material and a core-wrap sheet 41 overlying the skin-facing surface and the non-skin-facing surface of the absorbent core 40. The absorbent core 40 and the core-wrap sheet 41 are joined with a known joining means such as a hot melt adhesive. The absorbent core 40 is narrow in the central part in the length direction, or the longitudinal direction X in such a plan view as shown in FIG. 1 and has a sandglass-like shape. The absorbent core 40 includes an accumulated core forming material containing an absorbent material. As the absorbent material, any materials commonly used as the forming material of such absorbent cores can be used without limitation, and examples include wood pulp, hydrophilic fibers such as synthetic fibers treated with a hydrophilizing agent, and water-absorbing polymer particles. The absorbent core 40 can be a fiber laminate of hydrophilic fibers or water-absorbing polymer particles supported on the fiber laminate. As the core-wrap sheet 41, a water-permeable sheet material can be used, and paper or nonwoven fabric can be used, for example. In the diaper 1, the core-wrap sheet 41 is a single continuous core-wrap sheet 41 having a width twice or more and three times or less the length of the absorbent core 40 in the lateral direction Y. The single core-wrap sheet 41, as shown in FIG. 2, overlies the whole region of the skin-facing surface of the absorbent core 40 and extends from the respective side edges of the absorbent core 40 along the longitudinal direction X outward in the lateral direction Y, and the extension portions are folded under the absorbent core 40 and overlie the whole region of the non-skin-facing surface of the absorbent core 40. The configuration of the core-wrap sheet 41 is not limited to the above. For example, the core-wrap sheet may include a skin-facing core-wrap sheet overlying the skin-facing surface of the absorbent core 40 and a non-skin-facing core-wrap sheet overlying the non-skin-facing surface of the absorbent core 40, and the two sheets may be separate sheets.

As shown in FIG. 1, in each waist part of the front portion A and the rear portion C, or between the topsheet 2 and the backsheet 5 in each edge part in the longitudinal direction X, a continuous elastic member 11 is fixed in a stretched state in the lateral direction Y over substantially the entire length of the diaper 1 in the lateral direction Y. Accordingly, in the waist part at the time of wearing of the diaper 1, the elastic members 11 contract to form waist gathers. Between the topsheet 2 and the backsheet 5 in the hip part corresponding to the hips of a wearer in the rear portion C, a plurality of filamentous elastic members 12 are fixed in a stretched state in the lateral direction Y. Accordingly, in the hip part at the time of wearing of the diaper 1, the elastic members 12 contract to form hip gathers. Between leak-proof cuff-forming sheets 60 in right and left leg parts to be provided around the legs of a wearer and the backsheet 5, filamentous elastic members 13 are fixed in a stretched state along the longitudinal direction X. Accordingly, in the leg parts at the time of wearing of the diaper 1, the elastic members 13 contract to form a pair of leg gathers. The topsheet 2, the sublayer 3, the backsheet 5, the absorbent member 4, the sheets 60, and the elastic members 11 to 13 are joined to each other by a known joining means such as a hot melt adhesive.

The diaper 1, as shown in FIG. 1 and FIG. 2, includes a pair of leak-proof cuffs 6, 6 that are provided along the respective ends of the absorbent member 4 in the lateral direction Y and are to rise toward the skin of a wearer in at least the crotch portion B at the time of wearing of the diaper 1. Each of the leak-proof cuffs 6, 6 includes a hydrophobic, leak-proof cuff-forming sheet 60 extending over the entire length of the diaper 1 in the longitudinal direction X and one or a plurality of (two in the present embodiment) filamentous, leak-proof cuff-forming elastic members 61 that are fixed to the sheet 60 in a stretched state in the longitudinal direction X. The leak-proof cuff-forming sheet 60 is provided so as to straddle a side edge 4S along the longitudinal direction X of the absorbent member 4 in the lateral direction Y. In the diaper 1 in such a flat-out, uncontracted state as shown in FIG. 1, an outer side edge along the longitudinal direction X of the sheet 60 is located outward from the side edge 4S in the lateral direction Y, and an inner side edge along the longitudinal direction X of the sheet 60 is located inward form the side edge 4S in the lateral direction Y. The sheet 60 is joined, outside the side edge 4S in the lateral direction Y, to other members such as the topsheet 2 and the backsheet 5 to form a fixing part 62. In addition, to the inner side edge of the sheet 60, elastic members 61 are fixed in a stretched state in the longitudinal direction X. The inner side edge of the leak-proof cuff-forming sheet 60, in at least the crotch portion B, specifically, for example, in the crotch portion B and closer regions of the front portion A and the rear portion C to the crotch portion B, is a free end portion that is not joined to the topsheet 2, and, in the front and rear end portions in the longitudinal direction X of the front portion A and the rear portion C, the inner side edge is joined to the topsheet 2 (not shown). With the above structure, at the time of wearing of the diaper 1, the contraction force of the elastic members 61 in the longitudinal direction X allows the leak-proof cuffs 6 to rise in at least the crotch portion B, in which the inner side edge of each leak-proof cuff-forming sheet 60 is the free end portion, while the free end portions are toward the skin of a wearer from the fixing parts 62 as the starting point. Between the rising leak-proof cuffs 6 and the topsheet 2, a pocket is formed to effectively prevent excrements from leaking laterally in the crotch portion B. As the leak-proof cuff-forming sheets 60, a hydrophobic sheet material can be used, and as the sheet material, nonwoven fabrics, resin films, and laminates of them produced by various methods can be used, for example.

As shown in FIG. 1, to the respective lateral side edge portions along the longitudinal direction X in the rear portion C of the diaper 1, a pair of fastening tapes 7, 7 are provided. To each fastening tape 7, an attachment portion 71 including a male member of a mechanical hook and loop fastener is attached. On the non-skin-facing surface in the front portion A of the diaper 1, a target region 8 including a female member of the mechanical hook and loop fastener is formed. The target region 8 is formed by joining and fixing the female member of the mechanical hook and loop fastener to the non-skin-facing surface on the backsheet 5 constituting the non-skin-facing surface in the front portion A by using a known joining means such as an adhesive and heat sealing, and enables removable fastening of the attachment portion 71 of the fastening tape 7.

Figure 3:
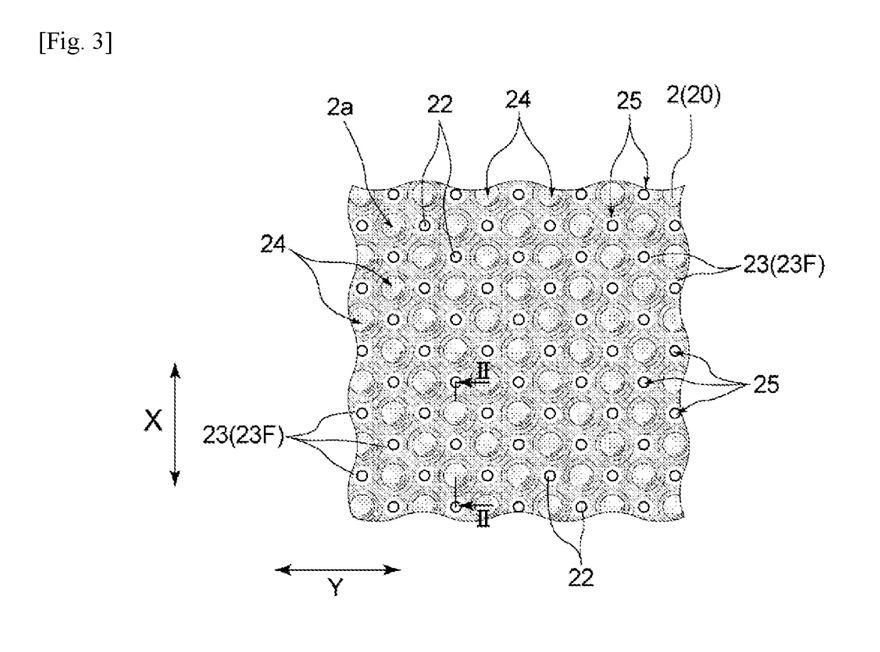
FIG. 3 is a schematic plan view showing a part of the skin-facing surface of the topsheet in the diaper shown in FIG. 1.
Figure 4:
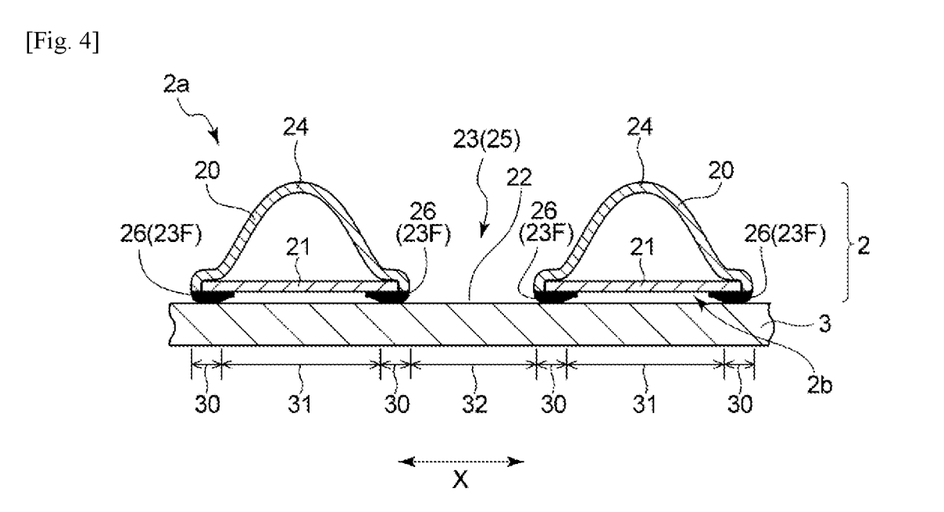
FIG. 4 is a schematic sectional view showing a cross section taken along line II-II in FIG. 3.
Figure 5:
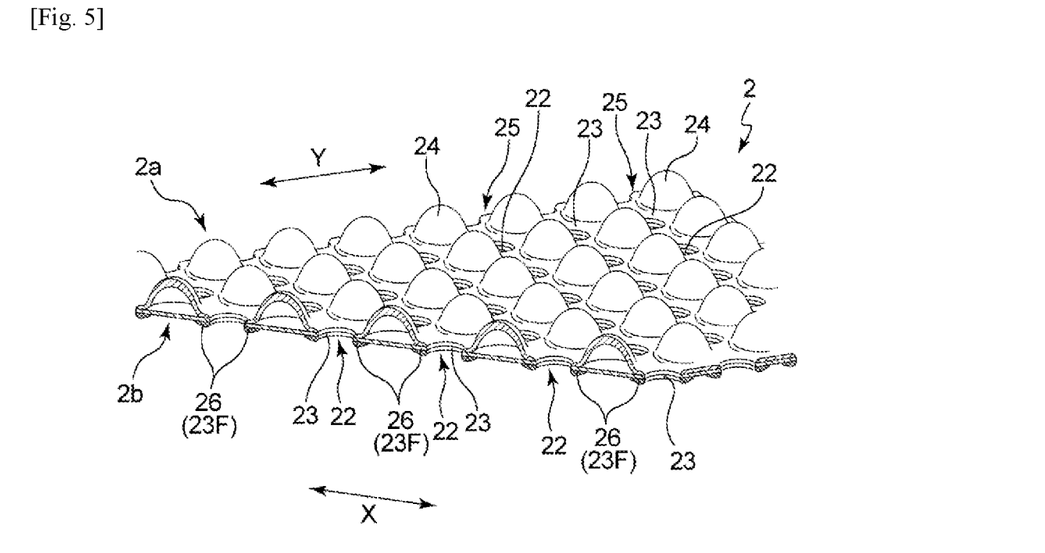
FIG. 5 is a schematic perspective view of the topsheet in the diaper shown in FIG. 1.

FIG. 3 to FIG. 5 show the topsheet 2, one of the main characteristic parts of the diaper 1. The topsheet 2, as shown in FIG. 2 to FIG. 5, includes a laminate of a first nonwoven fabric 20 and a second nonwoven fabric 21 and has a plurality of openings 22 penetrating the laminate in the thickness direction. The two nonwoven fabrics 20, 21 are fused together at peripheral edges of the openings 22 to form a plurality of fusion bond portions 23. The first nonwoven fabric 20 in a region other than the fusion bond portions 23 protrudes in a direction away from the second nonwoven fabric 21 to form a plurality of projections 24 protruding toward the skin of a wearer, thereby forming a three-dimensional perforated sheet.

In the topsheet 2, the first nonwoven fabric 20 is located at the side relatively close to the skin of a wearer, and the second nonwoven fabric 21 is located at the side relatively distant from the skin of a wearer. The two nonwoven fabrics 20, 21 are integrated in the thickness direction by the partially formed fusion bond portions 23 to constitute the laminate of the two nonwoven fabrics 20, 21. In the first nonwoven fabric 20, portions positioned among the plurality of fusion bond portions 23 (openings 22) convexly project in the direction opposite to the second nonwoven fabric 21 to form a plurality of hollow projections 24. In the topsheet 2, the side on the second nonwoven fabric 21, or the non-skin-facing surface 2b, is substantially flat, and on the side on the first nonwoven fabric 20, or the skin-facing surface 2a, the projections 24 and the other regions (opening 22 and fusion bond portions 23) constitute unevenness with large roughness.

The topsheet 2 has, in the sheet plane, a first direction X and a second direction Y orthogonal thereto. When the topsheet is integrated in the diaper 1, the first direction X is coincident with the longitudinal direction X, or the length direction, of the diaper 1, and the second direction Y is coincident with the lateral direction Y, or the width direction, of the diaper 1.

Typically, the first direction X of the topsheet 2 is coincident with the delivery direction of an original fabric of the first nonwoven fabric 20 and the second nonwoven fabric 21, and with the conveyance direction (MD) at the time of production of the topsheet 2 in many cases. Typically, when the first nonwoven fabric 20 and the second nonwoven fabric 21 are, for example, a nonwoven fabric, the first direction X of the topsheet 2 is coincident with the main fiber orientation direction of constituent fibers of the two nonwoven fabrics 20, 21 in many cases.

As shown in FIG. 3 to FIG. 5, each opening 22 is provided on the bottom part 25 among the plurality of projections 24 and is surrounded by a fusion bond portion 23. Each opening 22 is formed inside the corresponding fusion bond portion 23 and penetrates the first nonwoven fabric 20 and the second nonwoven fabric 21. The shape of each opening 22 in a plan view is a similar figure formed by uniformly reducing the shape of the fusion bond portion 23, and in the present embodiment, the shape is a round shape as shown in FIG. 3. However, the shape of each fusion bond portion 23 in a plan view is not limited to the round shape but can be freely set. Examples of the shape include a rectangular shape, a track shape, and regular polygonal shapes.

Each fusion bond portion 23 has a film portion 23F formed by making constituent fibers of the topsheet 2 into a film. In the description, being made into a film means such a state that constituent fibers in a topsheet 2 are uniformly melted together without clearance to be fused until no fiber shape of the constituent fibers is observed and a liquid is unlikely to penetrate the resulting film. The film portion 23F is a portion in which constituent fibers are melted and solidified and thus is harder and has a higher rigidity than the other portions not made into a film. A part or all of the fusion bond portion 23 can be the film portion 23F, and the distribution of the film portion 23F is affected by conditions of heating and pressing when the fusion bond portion 23 is formed, types of nonwoven fabrics 20, 21, and the like. An example of a typical state include a configuration in which the peripheral edge of the opening 22 and the vicinity thereof are the film portion 23F, and the other region, for example, a region comparatively close to the inner space of the projection 24 is not completely made into a film.

The cross-section shape of each projection 24 is preferably a dome shape having a smooth round ridge as a whole, a flat, rectangular parallelepiped shape, a truncated quadrangular pyramid shape, or the like. In the embodiment, the topsheet 2 has a round dome shape as shown in FIG. 4 and FIG. 5.

In the present invention, the openings 22, the fusion bond portions 23 around the openings, and the projections 24 can be dispersed on the topsheet 2 in the in-plane direction. In the present embodiment, they are equally dispersed on the topsheet 2 in the in-plane direction. Specifically, as shown in FIG. 3, the openings 22 together with the peripheral fusion bond portions 23 and the projections 24 are alternately aligned in the longitudinal direction X. The opening 22 together with the peripheral fusion bond portions 23 and the projections 24 are also alternately aligned in the lateral direction Y. The opening 22 together with the peripheral fusion bond portions 23 are aligned in a direction inclined to the longitudinal direction X and the lateral direction Y while spaced at regular intervals. The projections 24 are also aligned in a direction inclined to the longitudinal direction X and the lateral direction Y while spaced at regular intervals. Between adjacent lines in the lateral direction Y in which openings 22 with peripheral fusion bond portions 23 and projections 24 are alternately aligned in the longitudinal direction X, the positions of the openings 22 together with the peripheral fusion bond portions 23 are displaced by a half pitch in the longitudinal direction X, and the positions of the projections 24 are also displaced by a half pitch in the longitudinal direction X. Between adjacent lines in the longitudinal direction X in which openings 22 with peripheral fusion bond portions 23 and projections 24 are alternately aligned in the lateral direction Y, the positions of the opening 22 together with the peripheral fusion bond portions 23 are displaced by a half pitch in the lateral direction Y, and the positions of the projections 24 are also displaced by a half pitch in the lateral direction Y.

Examples of the nonwoven fabric constituting the first nonwoven fabric 20 and the second nonwoven fabric 21 include an air-through nonwoven fabric, a spunbonded nonwoven fabric, a spunlace nonwoven fabric, a meltblown nonwoven fabric, a resin bonded nonwoven fabric, and a needle punching nonwoven fabric. A laminate of two or more such nonwoven fabrics in combination or a laminate of such a nonwoven fabric and a film or the like in combination can also be used. Of them, an air-through nonwoven fabric or a spunbonded nonwoven fabric is preferably used. Each of the first nonwoven fabric 20 and the second nonwoven fabric 21 preferably has a basis weight of 7 g/m$^2$ or more, more preferably 10 g/m$^2$ or more, and preferably 40 g/m$^2$ or less, more preferably 35 g/m$^2$ or less.

The constituent fibers of the first nonwoven fabric 20 and the second nonwoven fabric 21 preferably have a fiber diameter of 0.5 dtex or more, more preferably 1.0 dtex or more, and preferably 4.0 dtex or less, more preferably 3.0 dtex or less, from the viewpoint of improvement in texture, for example.

The constituent fibers of the first nonwoven fabric 20 and the second nonwoven fabric 21 are made from a thermoplastic resin. Examples of the thermoplastic resin include a polyolefin resin, a polyester resin, a polyamide resin, an acrylonitrile resin, a vinyl resin, and a vinylidene resin. Examples of the polyolefin resin include polyethylene, polypropylene, and polybutene. Examples of the polyester resin include polyethylene terephthalate and polybutylene terephthalate. Examples of the polyamide resin include nylon. Examples of the vinyl resin include polyvinyl chloride. Examples of the vinylidene resin include polyvinylidene chloride. Such various resins can be used singly or as a mixture of two or more of them. Modified products of such various resins can also be used. Such various resins are preferably a resin containing one or more of a homopolymer, a random copolymer, and a block copolymer at 50 to 100% by mass. A resin mixture of such a homopolymer, a random copolymer, and a block copolymer can also be used. From the viewpoint of improvement in peel strength between the first nonwoven fabric 20 and the second nonwoven fabric 21, the first nonwoven fabric 20 and the second nonwoven fabric 21 are preferably constituted from the same thermoplastic resin.

The constituent fibers of the first nonwoven fabric 20 and the second nonwoven fabric 21 are preferably subjected to hydrophilization treatment. If the constituent fibers are weakly hydrophilic or hydrophobic, the liquid permeability that is one essential property for the topsheet 2 may be insufficient. The hydrophilization treatment can be any treatment commonly performed for such absorbent articles, and examples include a treatment of applying a hydrophilizing agent such as a surfactant onto the fiber surface, kneading of a hydrophilizing agent into fibers, corona discharge treatment, and plasma discharge treatment. Two or more of these treatments may be performed in combination.

Between the first nonwoven fabric 20 and the second nonwoven fabric 21, the hydrophilicities of the constituent fibers may be the same or different. In the latter case, the second nonwoven fabric 21 has a higher hydrophilicity than that of the first nonwoven fabric 20 in an embodiment. In the description, the hydrophilicity is determined on the basis of a contact angle with water measured by the method described below. A smaller contact angle with water indicates a higher hydrophilicity (lower hydrophobicity), whereas a higher contact angle with water indicates a lower hydrophilicity (higher hydrophobicity). A fabric having a contact angle with water of less than 90 degrees is hydrophilic, whereas a fabric having a contact angle with water of not less than 90 degrees is hydrophobic. A second nonwoven fabric 21 having a higher hydrophilicity than that of a first nonwoven fabric 20 means that the second nonwoven fabric 21 has a smaller contact angle with water than that of the first nonwoven fabric 20.

<Measurement Method of Contact Angle>

From a measurement object (nonwoven fabric), a fiber is sampled, and the contact angle of water to the fiber is measured. As the measurement device, an automatic contact angle meter, MCA-J, manufactured by Kyowa Interface Science Co., Ltd. is used. To measure contact angles, distilled water is used. The liquid amount ejected from an inkjet type water droplet ejection unit (manufactured by Cluster Technology Co., Ltd., a pulse injector, CTC-25, having an ejection unit pore size of 25 μm) is set to 20 picoliters, and a water drop is dropped directly above the fiber. The dropping state is recorded with a high-speed video recorder connected to a camera installed horizontally. The video recorder is preferably a personal computer integrated with a high-speed capturing apparatus from the viewpoint of subsequent image analysis. In the measurement, images are recorded every 17 msec. Of the recorded images, the first image in which a water drop reaches a fiber is subjected to image analysis using an attachment software, FAMAS (ver. 2.6.2; analytical technique, droplet; analytical method, θ/2; image processing algorithm, non-reflecting; image processing mode, frame; threshold level, 200; without curvature correction) to calculate the angle between the face of the water drop in contact with air and the fiber to give a contact angle. The fiber sampled from a measurement object is cut into a fiber length of 1 mm, and the cut fiber is placed on a sample table of a contact angle meter and is held horizontally. For a single fiber, contact angles are measured at different two sites. Contact angles of five fiber are measured to one decimal place, and the average of the measured values at 10 sites in total (rounded to one decimal place) is defined as the contact angle with water of the fibers. The measurement environment is a room temperature of 22±2° C. and a humidity of 65±2% RH.

One of the main characteristics of the diaper 1 is that, as shown in FIG. 4 and FIG. 5, the fusion bond portions 23 of the topsheet 2 have protrusions 26 protruding toward the sublayer 3 (protruding toward the side opposite to the projections 24), and a plurality of the protrusions 26 are dispersed on the surface facing the sublayer 3, or the non-skin-facing surface 2b of the topsheet 2. Each protrusion 26 is located at a site corresponding to the peripheral edge of the corresponding projection 24, on the non-skin-facing surface 2b of the topsheet 2 (the non-skin-facing surface of the second nonwoven fabric 21) (in a plan view as shown in FIG. 3, a site overlapping with the peripheral edge of the projection 24), and protrudes closer to the sublayer 3 than the periphery, and at least the tip in the protruding direction can be in contact with the sublayer 3.

In the diaper 1 having such a characteristic structure, when the topsheet 2 is pressed against the sublayer 3, specifically, for example, when the body pressure of a wearer is applied to the topsheet 2 at the time of wearing of the diaper 1, the sublayer 3 is partly pressed by the protrusions 26 on the topsheet 2. The regions in the sublayer 3 pressed by the protrusions 26 have a higher fiber density of constituent fibers than the other regions without pressure by the protrusions 26. As a result, in the condition in which the body pressure of a wearer is applied to the topsheet 2, high fiber density portions 30 having a relatively high fiber density are formed in regions corresponding to the protrusions 26 in the sublayer 3 as shown in FIG. 4, and low fiber density portions 31 having a relatively low fiber density are formed in the other regions (regions without pressure by the protrusions 26). The low fiber density portions 31 overlap with the forming positions of the projections 24 and at least overlap with the tops and vicinities of the projections 24.

The diaper 1, which has such a characteristic structure, can exert excellent absorbability to both low viscosity excrements and high viscosity excrements.

In other words, for low viscosity excrements such as urine, capillary force is likely to be effective, and such excrements are likely to move to portions having a high fiber density. When a conventional topsheet having openings, fusion bond portions around the openings, and projections protruding toward the skin of a wearer is used in combination with a sublayer, the absorbability of high viscosity excrements such as loose feces are secured by the openings and the sublayer. However, the whole topsheet is a high fiber density portion, whereas the whole sublayer is a low fiber density portion, and thus a density gradient is formed. Accordingly, low viscosity excrements may be difficult to move to the sublayer.

In contrast, in the diaper 1, as described above, the protrusions 26 of the topsheet 2 partly press the sublayer 3 at the time of wearing, and high fiber density portions 30 are formed, in the sublayer 3, with a pattern corresponding to the pattern of the pressed portions (protrusions 26). As a result, a plurality of high fiber density portions 30 and low fiber density portions 31 are dispersed in the sublayer 3 in the in-plane direction, thus while the absorbability of high viscosity excrements are maintained by the low fiber density portions 31, drawability of low viscosity excrements can be achieved by the high fiber density portions 30, and excellent absorbability can be exerted for both low viscosity excrements and high viscosity excrements.

The topsheet 2 has the multilayer structure including the first nonwoven fabric 20 on which unevenness is formed and the planar second nonwoven fabric 21 on which no unevenness is formed to give substantially no unevenness, thus has higher shape retention properties of the openings 22 than a topsheet including a single nonwoven fabric with unevenness such as the topsheet disclosed in Patent Literature 1, and is unlikely to cause the openings 22 to be closed. Hence, the diaper 1 certainly exerts advantageous effects by the openings 22 including quick drawing of excrements, specifically, high viscosity excrements, reduction in remaining liquid on the skin-facing surface 2a due to the drawing, and prevention of liquid returning. In addition, when the body pressure of a wearer is applied to the topsheet 2, the pressure is concentrated at the second nonwoven fabric 21, accordingly the protrusions 26 certainly press the sublayer 3, and the high fiber density portions 30 and the low fiber density portions 31 are stably formed in the sublayer 3 in the in-plane direction.

In order to more certainly exert the above advantageous effects, each portion of the topsheet 2 preferably has the following dimensions and the like.

Each opening 22 preferably has an opening area of 1 mm$^2$ or more, more preferably 2 mm$^2$ or more, and preferably 100 mm$^2$ or less, more preferably 50 mm$^2$ or less.

Each opening 22 preferably has a major axis length of 1 mm or more, more preferably 2 mm or more, and preferably 10 mm or less, more preferably 7 mm or less. In the description, the major axis length of the opening 22 means the maximum distance across the opening 22. When the opening 22 has a round shape in a plan view as shown in FIG. 3, the major axis length is the diameter.

The number of openings 22 per unit area (1 cm$^2$) is preferably one or more, more preferably four or more, and preferably 50 or less, more preferably 30 or less.

The fusion bond portions 23 having the corresponding protrusions 26 are formed around the openings 22, and thus the number and arrangement of the fusion bond portions 23 (protrusions 26) basically correspond to the number and arrangement of the openings 22.

Each projection 24 preferably has a height of 1 mm or more, more preferably 3 mm or more, and preferably 20 mm or less, more preferably 15 mm or less.

Each projection 24 in such a plan view as shown in FIG. 3 preferably has an area (bottom area) of 1 mm$^2$ or more, more preferably 4 mm$^2$ or more, and preferably 400 mm$^2$ or less, more preferably 300 mm$^2$ or less.

The number of projections 24 per unit area (1 cm$^2$) is preferably one or more, more preferably three or more, and preferably 15 or less, more preferably 12 or less.

In the present embodiment, each protrusion 26 has a film portion 23F. The film portion 23F has a higher rigidity than the other portions in the topsheet 2 not made into a film. The protrusion 26 having the film portion 23F has a higher rigidity, and the protrusion 26 hardens. Accordingly, the pressing force by the protrusions 26 against the sublayer 3 is increased, and consequently, the fiber density gradient in the sublayer 3 in the in-plane direction is more certainly formed. This results in further improvement in absorbability for both low viscosity excrements and high viscosity excrements. A part or all of each protrusion 26 can be the film portion. In order to more certainly exert the above advantageous effects, at least the tip of the protrusion 26 in the protruding direction toward the sublayer 3 is preferably the film portion 23F.

Figure 6:
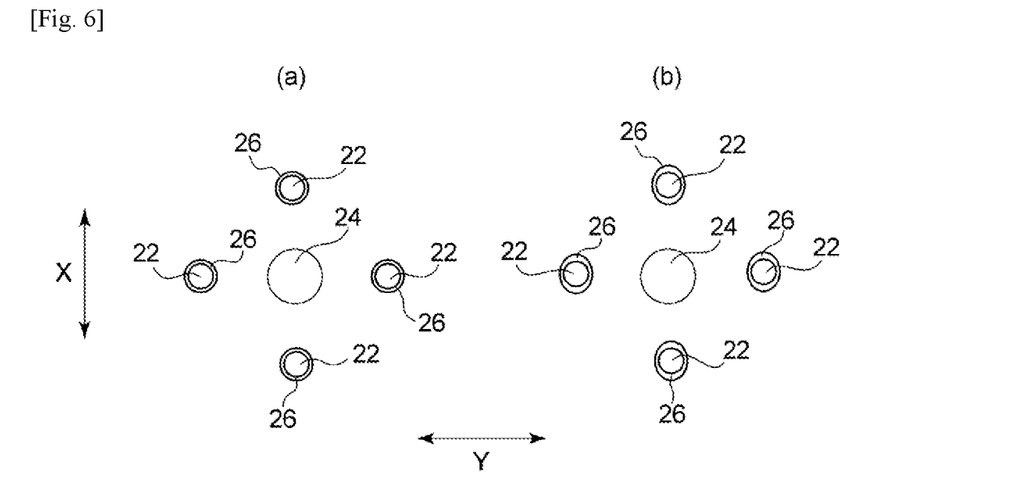
FIG. 6(a) and FIG. 6(b) are enlarged schematic plan views showing a part of a non-skin-facing surface (sublayer-facing surface) of the topsheet pertaining to the present invention and are views showing the distribution state of protrusions of fusion bond portions around openings.

Each protrusion 26 may be formed in an entirely uniform size around the opening 22 as shown in FIG. 6(a) or may be formed in uneven distribution or an uneven size around the opening 22 as shown in FIG. 6(b). Typically, a protrusion 26 having a larger size has a larger contact area with the sublayer 3, and thus the fiber density gradient in the sublayer 3 in the in-plane direction is likely to be caused. Hence, the protrusions are preferably large from the viewpoint of the absorbability of the diaper 1 for excrements. However, the protrusions 26 are a melted and solidified product of a forming material (thermoplastic resin) in the peripheral edge of the openings 22, and the forming material of the protrusions 26 is finite in consideration of the balance with other portions including the openings 22. Hence, an entirely, comparatively large protrusion 26 evenly formed around the opening 22 as shown in FIG. 6(a) may cause unfavorable effects on other portions including the opening 22 of the topsheet 2. When a comparatively large protrusion 26 is intended to be provided, such comparatively large parts of the protrusion 26 are preferably, unevenly distributed at a part of the circumference of the openings 22 as shown in FIG. 6(b). With such a configuration, a finite forming material of each protrusion 26 can be selectively allocated in intended regions around the opening 22, and the protrusion 26 can be enlarged in the regions. As a result, a high fiber density portion 30 having a comparatively large size is formed in the sublayer 3 corresponding to such comparatively large parts of the protrusion 26, and this especially improves the absorbability for low viscosity excrements such as urine.

An example of the uneven distribution of a protrusion 26 is, as shown in FIG. 6(b), a configuration in which the forming material (thermoplastic resin) of the protrusion 26 is unevenly distributed at both longitudinal sides of the opening 22 in longitudinal direction X, and the forming material is absent at both lateral sides of the opening 22, or an amount of the forming material of the opening 22 is smaller at the both lateral sides in the lateral direction Y than at the longitudinal sides in longitudinal direction X. In such a configuration as shown in FIG. 6(b), each protrusion 26 is unevenly distributed in the longitudinal direction X coincident with the front-to-rear direction of a wearer wearing the diaper 1. Hence, in the sublayer 3 pressed by such protrusions 26 unevenly distributed in the longitudinal direction X, high fiber density portions 30 having a comparatively large area are intermittently arranged in the longitudinal direction X, and this especially improves the diffusibility of low viscosity excrements that are likely to be drawn into the high fiber density portions 30, such as urine, in the longitudinal direction X to result in prevention of excrement lateral leakage or effective utilization of the absorbent member 4. Such uneven distribution of protrusions 26 around the corresponding openings 22 can be achieved by a technique of a conveyance manner of a second nonwoven fabric 21 to form openings 22 at the time of production of a topsheet 2. This technique will be described later.

Figure 7:
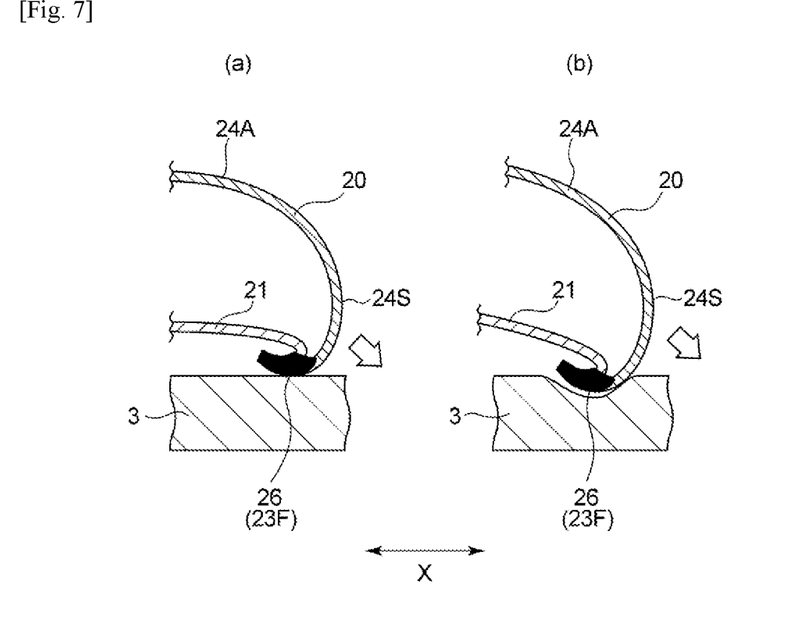
FIG. 7(a) is a view partly showing an embodiment of the projection pertaining to the topsheet pertaining to the present invention and corresponding to FIG. 4.
FIG. 7(b) is a schematic view showing the projection when the topsheet having the projection shown in FIG. 7(a) is pressed from the skin-facing surface.

FIG. 7 shows a projection 24A as a preferred embodiment the projections of the topsheet pertaining to the present invention. In order to certainly form density gradient effective in improving the absorbability of the sublayer 3 in the in-plane direction for low viscosity excrements, the protrusion 26 preferably has a film portion 23F. The film portion 23F however has no liquid permeability, and thus the protrusion 26 itself having the film portion has low liquid permeability. This is not considered to be preferred from the viewpoint of liquid permeability from the topsheet 2 to the sublayer 3. However, as for the projection 24A in its natural state, in a cross section of the topsheet 2 in a certain direction in the in-plane direction (for example, the longitudinal direction X), the outermost edge 24S in the certain direction is located outward in the certain direction from the protrusion 26 near the projection 24A as shown in FIG. 7(a). Although the protrusion 26 has the film portion 23F and intrinsically has low liquid permeability, the liquid permeability from the topsheet 2 to the sublayer 3 is therefore improved.

In other words, for example, in such a case as shown in FIG. 7(a) in which the outermost edge 24S of the projection 24A in the longitudinal direction X in a cross section in the longitudinal direction X is located outward in the longitudinal direction X from the protrusion 26 near the projection 24A, when the projection 24A is pressed toward the sublayer 3 by, for example, the body pressure of a wearer wearing a diaper 1, the outermost edge 24S and the vicinity thereof come into contact with the sublayer 3 (the region in the sublayer 3 overlapping with the opening 22) as shown in FIG. 7(b). In this case, the projection 24A including the outermost edge 24S (in the first nonwoven fabric 20, a part located closer to the skin of a wearer than the second nonwoven fabric 21) is not made into a film but holds a fiber shape of constituent fibers. Hence, excrements are allowed to move through the contact part of the projection 24A with the sublayer 3 to the sublayer 3, and accordingly the liquid permeability from the topsheet 2 to the sublayer 3 is achieved. In addition, such contact of the projection 24A with the sublayer 3 compresses the contact part in the sublayer 3 with the projection 24A to reduce the distance between fibers in the contact part, and thus the permeability of low viscosity excrements such as urine is especially improved.

In order to more certainly exert such advantageous effects by the outermost edge 24S of the projection 24A, in a cross section of the topsheet 2 in any direction in the in-plane direction, the outermost edge 24S in the any direction is preferably located outward in the any direction from the protrusion 26 near the projection 24A. Location of the outermost edge 24S outward the protrusion 26 in any direction in the topsheet 2 in the in-plane direction as above can be achieved by selection of constituent fibers of a first nonwoven fabric 20 forming projections 24A, a technique of a conveyance manner of a first nonwoven fabric 20 at the time of production of a topsheet 2, or the like.

In the sublayer 3, portions 32 overlapping with the openings 22 (see FIG. 4) preferably have a larger average distance between fibers than that of the high fiber density portions 30 overlapping with the protrusions 26. With such a configuration, the high fiber density portions 30 in the sublayer 3 overlapping with the protrusions 26 have a relative small average distance between fibers to further improve especially the liquid permeability of low viscosity excrements such as urine, whereas the portions 32 in the sublayer 3 overlapping with the openings 22 have a relatively large average distance between fibers to further improve especially the liquid permeability of high viscosity excrements such as loose feces. Such a sublayer 3 having partly different average distances between fibers can be produced by the following manner: for example, a topsheet 2 and a sublayer 3 are bonded with an adhesive such as a hot melt adhesive to give a laminate; and the laminate is pressed in the thickness direction. The laminate can be pressed from either or both of the skin-facing surface and the non-skin-facing surface. By pressing the laminate, the average distance between fibers in portions of the sublayer 3 overlapping with protrusions 26 (high fiber density portions 30) is reduced relative to the other portions of the sublayer 3 (low fiber density portions 31). When the adhesive applied between the topsheet 2 and the sublayer 3 infiltrates and the pressed state by pressing is maintained, a sublayer 3 in which the portions 32 overlapping with the openings 22 have a larger average distance between fibers than that of the portions overlapping with the protrusions 26 (high fiber density portions 30) is produced. The average distance between fibers can be determined by the method below.

<Measurement Method of Average Distance Between Fibers in Sheet>

The average distance between fibers of a fiber aggregate such as a nonwoven fabric and paper is determined in accordance with Equation (1) based on a hypothesis by Wrotnowski. Equation (1) is typically used to determine the distance between fibers of a fiber aggregate. Under the hypothesis by Wrotnowski, a fiber has a column shape, and fibers do not intersect but are regularly arranged.

When a sheet (sublayer) as the measurement object has a single layer structure, the average distance between fibers of the sheet with the single layer structure is calculated in accordance with Equation (1).

When a sheet (sublayer) as the measurement object has such a multilayer structure as a known SMS nonwoven fabric, the average distance between fibers of the sheet with the multilayer structure is determined in accordance with the following procedure.

First, the average distance between fibers of each layer included in the multilayer structure is calculated in accordance with Equation (1). For the calculation, the thickness t, basis weight W, fiber density ρ, and fiber diameter D used in Equation (1) are those of a layer as the measurement object, and the thickness t is measured by microscope observation of a cross section of a layer as the measurement object in the thickness direction. Each of the thickness t, the basis weight W, and the fiber diameter D is an average of measured values at a plurality of measurement sites. The basis weight W (g/m²) is determined by the following procedure: a sheet as the measurement object is cut into a predetermined size and weighed; and the weighed value is divided by an area calculated from the predetermined size. The fiber density ρ (g/cm³) is determined by using a density gradient tube in accordance with measurement method by density gradient tube method described in JIS L1015, Test methods for man-made staple fibres (URL, http://kikakurui.com/l/L1015-2010-01.html, or JIS Handbook, Fibers-2000 (Japanese Standards Association), pages 764 to 765). The fiber diameter D (μm) is determined by using a scanning electron microscope (DSC6200 manufactured by Seiko Instruments) by the following procedure: fiber cross sections of 10 cut fibers are measured; and the average is calculated as the fiber diameter.

Next, the average distance between fibers of each layer is multiplied by the proportion of the thickness of the layer in the total thickness of the multilayer structure, and the calculated numerical values of the respective layers are summed up to give an average distance between fibers of constituent fibers in an intended sheet with a multilayer structure. For example, in an SMS nonwoven fabric with a three-layer structure including two S layers and one M layer, the two S layers are collectively handled as a single layer, and when the three-layer structure has a total thickness t of 0.11 mm, the S layer has a thickness t of 0.1 mm, the S layer has an average distance between fibers LS of 47.8 μm, the M layer has a thickness t of 0.01 mm, and the M layer has an average distance between fibers LS of 3.2 μm, the average distance between fibers of constituent fibers of the SMS nonwoven fabric is 43.8 μm [=(47.9×0.1+3.2×0.01)/0.11].

[Math. 1]

$$\text{Average distance between fibers (μm)} = 10^6 \sqrt{\frac{t \cdot \rho \cdot \pi D^2}{4 \cdot W \cdot 10^9}} - D \quad (1)$$

D: fiber diameter (μm)
ρ: fiber density (g/cm³)
t: thickness (mm)
w: basis weight (g/m²)

Figure 8:
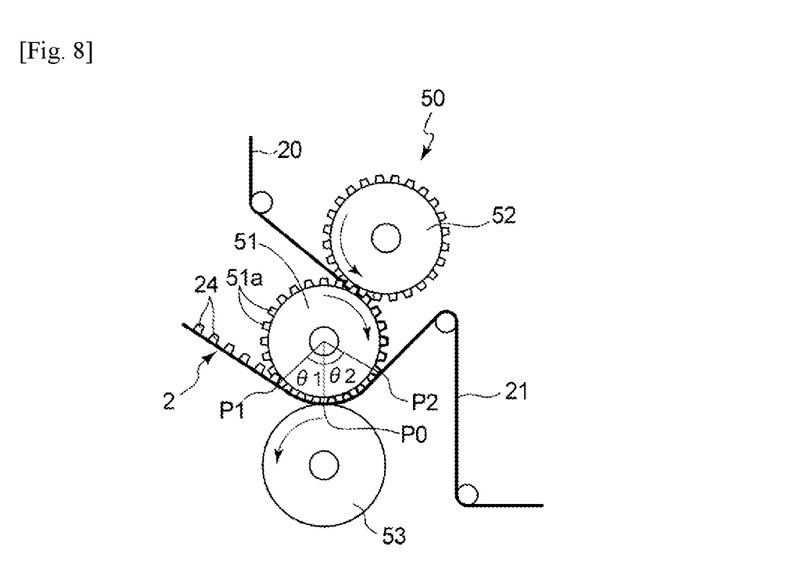
FIG. 8 is a schematic view showing an example of a production apparatus usable for production of the topsheet (three-dimensional perforated sheet) shown in FIG. 1.

The topsheet 2 can be produced by the method described below, for example. FIG. 8 shows a schematic diagram of a production apparatus 50 for a three-dimensional perforated sheet used in the production method of the present embodiment. The production apparatus 50 includes a first roller 51 on which a large number of projections 51a are formed on a peripheral surface to give an uneven shape on the peripheral surface, a second roller 52 having, on the peripheral surface, an uneven shape to engage with the uneven shape on the first roller 51, and an anvil roller (heat roller) 53 having a peripheral surface to face the peripheral surface of the first roller 51.

The first roller 51 has a plurality of voids (not shown) on the peripheral surface to come into contact with a first nonwoven fabric 20 as an article to be processed and includes an air suction mechanism (not shown) connected to the voids, and accordingly, suction from the inside of the roller enables the peripheral surface to hold the article to be processed. The second roller 52 has the same basic configuration as the first roller 51 but does not include such an air suction mechanism as included in the first roller 51, and accordingly, the peripheral surface cannot hold a sheet due to absence of suction from the inside of the roller. As the first roller 51 and the second roller 52 each having a peripheral surface with an uneven shape, the rollers disclosed in JP 2004-174234 A pertaining to a previous application by the present applicant can be used, for example. The anvil roller 53 has a cylindrical-shaped rotation body rotatably supported around a rotating shaft, and the peripheral surface of the rotation body is provided to face the peripheral surface of the first roller 51. The peripheral surface of the anvil roller 53 has no uneven shape and is substantially smooth. The anvil roller 53 is equipped with a heating means (not shown), and by heat conduction from the heating means, heat is conducted to the peripheral surface that is to come into contact with a second nonwoven fabric 21 as an article to be processed.

To produce the topsheet 2 as a three-dimensional perforated sheet, first, a first nonwoven fabric 20 is unreeled from an original fabric (not shown) of the first nonwoven fabric 20. Separately, a second nonwoven fabric 21 is unreeled from an original fabric (not shown) of the second nonwoven fabric 21. As shown in FIG. 8, the unreeled first nonwoven fabric 20 is bitten by an engagement portion between the first roller 51 and the second roller 52 to form unevenness on the first nonwoven fabric 20 (unevenness forming step). The first nonwoven fabric 20 adheres to the peripheral surface of the first roller 51 by suction force exerted on the peripheral surface of the first roller 51, and the formed unevenness state is maintained.

Next, while the first nonwoven fabric 20 with the formed unevenness is supported on the peripheral surface of the first roller 51, the second nonwoven fabric 21 is laminated on the first nonwoven fabric 20, then the second nonwoven fabric 21 is fused with the first nonwoven fabric 20 at positions corresponding to projections 51a of the first roller 51 to form fusion bond portions 23, and moreover, openings 22 are formed at forming positions of the fusion bond portions 23 (fusing and perforating step). Specifically, as shown in FIG. 8, while the first nonwoven fabric 20 is still supported by suction on the peripheral surface of the first roller 51, the second nonwoven fabric 21 is laminated, and the laminate of the two nonwoven fabrics 20, 21 is pressed between the first roller 51 and the anvil roller 53 with the smooth peripheral surface. In this step, both the first roller 51 and the anvil roller 53 or only the anvil roller 53 is previously heated at a predetermined temperature. Accordingly, the first nonwoven fabric 20 on projections 51a of the first roller 51 and the second nonwoven fabric 21 are joined by fusion bond to form fusion bond portions 23 and concurrently openings 22 are formed at forming positions in the fusion bond portions 23. In this step, a forming material (thermoplastic resin) at a contact part in each fusion bond portion 23 with the tip of a projection 51a is melted, and the melted material moves from the contact part to the periphery thereof to form the opening 22 at the contact part as the center. Depending on heating and pressing conditions in the fusing and perforating step, at least a part of the fusion bond portion 23 is made into a film portion 23F mainly in the vicinity of the opening 22.

Figure 9:
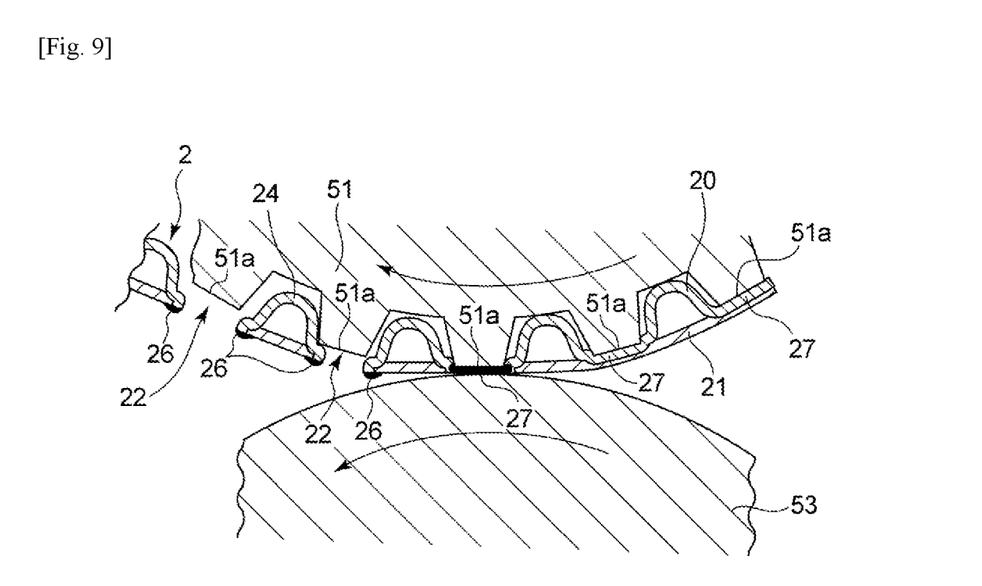
FIG. 9 is a view showing a fusing and perforating step using the production apparatus shown in FIG. 8.

The above steps are basically the same as in a known method for producing a three-dimensional perforated sheet disclosed in Patent Literature 2. One of the main features of the production method in the present embodiment relates to the formation of the protrusions 26 of the fusion bond portions 23. In other words, in the fusing and perforating step in the present embodiment, as shown in FIG. 9, brings the tip of the projection 51a of the first roller 51 into contact with the first nonwoven fabric 20 at a position 27 where the opening 22 in the laminate of the first nonwoven fabric 20 and the second nonwoven fabric 21 is to be formed, and concurrently, allows the projection 51a to penetrate a melted part of the fusion bond portion 23, so that a meltage of the fusion bond portion 23 is unevenly distributed on the side of the second nonwoven fabric 21 (the side of the anvil roller 53), thereby the protrusion 26 is formed. To simply form the opening 22, as in the related art, it is sufficient to bring the tip of the projection 51a on the first roller 51 into contact with the heated, formation intended position 27 of an opening. To form the protrusion 26 protruding toward the side opposite to the projections 24, the projection 51a used for the formation of an opening is required to be inserted into and to penetrate the opening 22 at the time of formation of the opening 22, or the tip of the projection 51a is required to be brought into contact with the counter peripheral surface of the anvil roller 53. By such perforating and penetrating of a roller projection, the meltage of the fusion bond portion 23 is extruded to the side of the second nonwoven fabric 21, and consequently the protrusion 26 is formed around the opening 22.

In order to certainly allow the projection 51a of the first roller 51 to penetrate the opening 22 and to stably form a protrusion 26, the outlet wrap angle θ1 of the second nonwoven fabric 21 to the first roller 51 (see FIG. 8) is preferably 5 degrees or more, more preferably 10 degrees or more. As shown in FIG. 8, in a cross section formed by cutting, on a flat surface orthogonal to the axis of the first roller 51, the first roller 51 and a second nonwoven fabric 21 as an article to be processed, when the downstream end in the region in which the second nonwoven fabric 21 is in contact with the peripheral surface of the first roller 51 (exactly, a first nonwoven fabric 20 supported on the peripheral surface of the first roller 51) is a downstream contact point P1, the outlet wrap angle θ1 means the angle between the straight line (line segment) between the downstream contact point P1 and the axis and the straight line (line segment) between the forming position P0 of the opening 22 (the nip portion between the projection 51a on the first roller 51 and the anvil roller 53) and the axis.

The two nonwoven fabrics 20, 21 are conveyed at respective predetermined tensions to the nip portion between the first roller 51 and the anvil roller 53, and on the way of the conveyance, fusion bond portions 23 and openings 22 are formed at the nip portion. As described above, when the outlet wrap angle θ1 of the second nonwoven fabric 21 to the first roller 51 is set to a comparatively large value, and the length of the second nonwoven fabric 21 (topsheet 2), which extends from the forming position of the opening 22 to the downstream side in the conveyance direction, on the peripheral surface of the first roller 51 in the circumferential direction is set to be comparatively large, the opening 22 is more certainly penetrated by the projection 51a, and protrusions 26 are more stably formed.

From a similar viewpoint, an inlet wrap angle θ2 of the second nonwoven fabric 21 to the first roller 51 (see FIG. 8) is preferably 5 degrees or more, more preferably 10 degrees or more. As shown in FIG. 8, in a cross section formed by cutting, on a flat surface orthogonal to the axis of the first roller 51, the first roller 51 and a second nonwoven fabric 21 as an article to be processed, when the upstream end in the region in which the second nonwoven fabric 21 is in contact with the peripheral surface of the first roller 51 (exactly, a first nonwoven fabric 20 supported on the peripheral surface of the first roller 51) is an upstream contact point P2, the inlet wrap angle θ2 means the angle between the straight line (line segment) between the upstream contact point P2 and the axis and the straight line (line segment) between the forming position P0 of the opening 22 and the axis.

The first roller 51 preferably has a radius of 30 mm or more, more preferably 50 mm or more, and preferably 300 mm or less, more preferably 200 mm or less.

As described above, uneven distribution of protrusions 26 at a part of the circumference of openings 22 can be achieved by adjustment of the conveyance speed of a second nonwoven fabric 21 or the like. For example, as shown in FIG. 6(b), to unevenly distributed material of the protrusion 26 at both longitudinal sides of the opening 22 in longitudinal direction X, the conveyance speed of the second nonwoven fabric 21 can be increased or reduced relative to the rotation speed of the first roller 51.

As described above, as shown in FIG. 7, in a cross section of the topsheet 2 in a certain direction in the in-plane direction, location of the outermost edge 24S in the certain direction outward in the certain direction from the protrusion 26 near the projection 24A can be achieved by selection of constituent fibers of the first nonwoven fabric 20 or adjustment of the conveyance manner of the first nonwoven fabric 20, for example. Specifically, for example, the second nonwoven fabric 21 to which tension is applied is fused with the first nonwoven fabric 20, and after the process with the first roller 51, the tension applied to the second nonwoven fabric 21 is released to allow the second nonwoven fabric 21 to shrink, and consequently the above location can be achieved.

The formation of a fusion bond portion 23 and the formation of the opening 22 are not simultaneously performed as above but can be performed separately. For example, a production apparatus in which an additional anvil roller (not shown) with a peripheral surface that faces the peripheral surface of a first roller 51 is provided at a downstream side of the sheet conveyance direction (MD) from the anvil roller 53 is used, a fusion bond portion 23 is first formed at a nip portion between the first roller 51 and the anvil roller 53, and the opening 22 is next formed in the fusion bond portion 23 at a nip portion between the first roller 51 and the additional anvil roller. In this case, in the forming process of openings 22, the above improvement relating to the formation of a protrusion 26 (perforating and penetrating by a roller projection, adjustment of wrap angles) is performed.

The present invention has been described on the basis of the embodiments, but the present invention can be appropriately modified without limitation by the embodiments. For example, from the viewpoint of improvement in absorbability, leak-proof performance, and the like, the skin-facing surface of the diaper 1 may have grooves that are formed by integral densification of the topsheet 2 and the absorbent member 4.

In the method for manufacturing a three-dimensional perforated sheet of the present invention, the method of fusing the first nonwoven fabric and the second nonwoven fabric (formation method of fusion bond portions) is not limited to such heating of articles to be processed as in the embodiment, but may be essentially a method of capable of melting the forming material of a nonwoven fabric, and sonication or the like may be used.

The present invention is not limited to such an open type disposable diaper as in the embodiment and widely encompasses articles used for absorption of body fluids excreted from a human body (such as urine, loose feces, menstrual blood, and sweat), and pull-on disposable diapers, sanitary napkins, sanitary shorts, and the like are also encompassed.

A portion only in one of the embodiments can be appropriately used exchangeably for another portion. In consideration of the above embodiments of the present invention, the following aspects are further disclosed.

<1> An absorbent article having a longitudinal direction coincident with a front-to-rear direction of a wearer and a lateral direction orthogonal to the longitudinal direction, the absorbent article comprising:
  a topsheet;
  a liquid-permeable sublayer; and
  a liquid-retentive absorbent member,
  the topsheet, the liquid-permeable sublayer, and the liquid-retentive absorbent member being sequentially stacked in increasing order of distance from a skin of a wearer, wherein
  the topsheet includes a laminate of a first nonwoven fabric and a second nonwoven fabric, the laminate has a plurality of openings penetrating the laminate in a thickness direction, the first nonwoven fabric and the second nonwoven fabric are fused together at peripheral edges of the openings to form a plurality of fusion bond portions, the first nonwoven fabric in a region other than the fusion bond portions protrudes in a direction away from the second nonwoven fabric to form a plurality of projections protruding toward a skin of a wearer,
  each fusion bond portion of the topsheet has a protrusion protruding toward the sublayer, and a plurality of the protrusions are dispersed on a surface of the topsheet facing the sublayer, and
  when the topsheet is pressed toward the sublayer, the sublayer is partially pressed by the protrusions of the topsheet.

<2> The absorbent article as set forth in clause <1>, wherein a forming material of the protrusion is unevenly distributed at a part of the circumference of the opening.

<3> The absorbent article as set forth in clause <1> or <2>, wherein the forming material of the protrusion is unevenly distributed at both longitudinal sides of the opening, and
  the forming material is absent at both lateral sides of the opening, or
  an amount of the forming material of the opening is smaller at the both lateral sides than at the longitudinal sides.

<4> The absorbent article as set forth in any one of clauses <1> to <3>, wherein in a cross section of the topsheet in a certain direction in an in-plane direction, an outermost edge of the projection in the certain direction is located outward in the certain direction from the protrusion in vicinity of the projection.

<5> The absorbent article as set forth in any one of clauses <1> to <4>, wherein in a cross section of the topsheet in the longitudinal direction, an outermost edge of the projection in the longitudinal direction is located outward in the longitudinal direction from the protrusion in vicinity of the projection.

<6> The absorbent article as set forth in any one of clauses <1> to <5>, wherein in a cross section of the topsheet in any direction in an in-plane direction, an outermost edge of the projection in the any direction is located outward in the any direction from the protrusion in vicinity of the projection.

<7> The absorbent article as set forth in any one of clauses <1> to <6>, wherein one of the openings is formed inside each of the plurality of fusion bond portions and penetrates the first nonwoven fabric and the second nonwoven fabric.

<8> The absorbent article as set forth in clause <7>, wherein a shape of the opening in a plan view is a similar figure formed by uniformly reducing a shape of the fusion bond portion in a plan view.

<9> The absorbent article as set forth in any one of clauses <1> to <8>, wherein the fusion bond portion has a film portion formed by making constituent fibers of the topsheet into a film.

<10> The absorbent article as set forth in clause <9>, wherein a peripheral edge of the opening and a vicinity thereof are the film portion, and another region in the topsheet is not made into a film.

<11> The absorbent article as set forth in clause <9> or <10>, wherein a tip of the protrusion in a protruding direction toward the sublayer is the film portion.

<12> The absorbent article as set forth in any one of clauses <1> to <11>, wherein in the sublayer, portions overlapping with the openings have a larger average distance between fibers than that of portions overlapping with the protrusions.

<13> The absorbent article as set forth in any one of clauses <1> to <12>, wherein in a condition in which a body pressure of a wearer is applied to the topsheet, high fiber density portions having a relatively high fiber density are formed in the sublayer in regions corresponding to the protrusions, concurrently low fiber density portions having a relatively low fiber density are formed in other regions of the sublayer, and the low fiber density portions overlap with forming positions of the projections.

<14> The absorbent article as set forth in any one of clauses <1> to <13>, wherein the opening has an opening area of preferably 1 $mm^2$ or more and more preferably 2 $mm^2$ or more, and preferably 100 $mm^2$ or less and more preferably 50 $mm^2$ or less.

<15> The absorbent article as set forth in any one of clauses <1> to <14>, wherein the opening has a major axis length of preferably 1 mm or more and more preferably 2 mm or more, and preferably 10 mm or less and more preferably 7 mm or less.

<16> The absorbent article as set forth in any one of clauses <1> to <15>, wherein a number of the openings per unit area of 1 $cm^2$ is preferably 1 or more and more preferably 4 or more, and preferably 50 or less and more preferably 30 or less.

<17> The absorbent article as set forth in any one of clauses <1> to <16>, wherein the projection has a height of preferably 1 mm or more and more preferably 3 mm or more, and preferably 20 mm or less and more preferably 15 mm or less.

<18> The absorbent article as set forth in any one of clauses <1> to <17>, wherein the projection in a plan view has an area (bottom area) of preferably 1 $mm^2$ or more and more preferably 4 $mm^2$ or more, and preferably 400 $mm^2$ or less and more preferably 300 $mm^2$ or less.

<19> The absorbent article as set forth in any one of clauses <1> to <18>, wherein a number of the projections per unit area of 1 $cm^2$ is preferably 1 or more and more preferably 3 or more, and preferably 15 or less and more preferably 12 or less.

<20> The absorbent article as set forth in any one of clauses <1> to <19>, wherein each of the first nonwoven fabric and the second nonwoven fabric includes an air-through nonwoven fabric or a spunbonded nonwoven fabric.

<21> The absorbent article as set forth in any one of clauses <1> to <20>, wherein each of the first nonwoven fabric and the second nonwoven fabric has a basis weight of preferably 7 $g/m^2$ or more and more preferably 10 $g/m^2$ or more, and preferably 40 $g/m^2$ or less and more preferably 35 $g/m^2$ or less.

<22> The absorbent article as set forth in any one of clauses <1> to <21>, wherein constituent fibers of the first nonwoven fabric and the second nonwoven fabric have a fiber diameter of preferably 0.5 dtex or more and more preferably 1.0 dtex or more, and preferably 4.0 dtex or less and more preferably 3.0 dtex or less.

<23> The absorbent article as set forth in any one of clauses <1> to <22>, wherein the sublayer is an air-through nonwoven fabric, a resin bonded nonwoven fabric, or an airlaid nonwoven fabric.

<24> The absorbent article as set forth in any one of clauses <1> to <23>, wherein the sublayer has a basis weight of preferably 10 g/m$^2$ or more and more preferably 15 g/m$^2$ or more, and preferably 100 g/m$^2$ or less and more preferably 70 g/m$^2$ or less.

<25> The absorbent article as set forth in any one of clauses <1> to <24>, wherein in the first nonwoven fabric, portions positioned among the plurality of fusion bond portions convexly project in a direction opposite to the second nonwoven fabric to form the plurality of hollow projections.

<26> The absorbent article as set forth in any one of clauses <1> to <25>, wherein in the topsheet, a side on the second nonwoven fabric or a non-skin-facing surface side is substantially flat, and on a side on the first nonwoven fabric or on a skin-facing surface side, the projections, the openings, and the fusion bond portions constitute unevenness with large roughness.

<27> The absorbent article as set forth in any one of clauses <1> to <26>, wherein
the topsheet has, in a sheet plane thereof, a first direction and a second direction orthogonal thereto, in the absorbent article, the first direction is coincident with the longitudinal direction of the absorbent article, and the second direction is coincident with the lateral direction of the absorbent article, and
the first direction of the topsheet is coincident with a main fiber orientation direction of constituent fibers of the first nonwoven fabric and the second nonwoven fabric.

<28> The absorbent article as set forth in any one of clauses <1> to <27>, wherein the openings together with the peripheral fusion bond portions and the projections are alternately aligned in both the longitudinal direction and the lateral direction.

<29> The absorbent article as set forth in any one of clauses <1> to <28>, wherein the openings together with the peripheral fusion bond portions are aligned in a direction inclined to the longitudinal direction and the lateral direction while spaced at regular intervals, and the projections are aligned in a direction inclined to the longitudinal direction and the lateral direction while spaced at regular intervals.

<30> A method for manufacturing a three-dimensional perforated sheet, the three-dimensional perforated sheet including a laminate of a first nonwoven fabric and a second nonwoven fabric, the laminate having a plurality of openings penetrating the laminate in a thickness direction, the first nonwoven fabric and the second nonwoven fabric being fused together at peripheral edges of the openings to form a plurality of fusion bond portions, the first nonwoven fabric in a region other than the fusion bond portions forming a plurality of projections protruding in a direction away from the second nonwoven fabric, each fusion bond portion having a protrusion protruding toward a side opposite to the projections,
the method comprising:
an unevenness forming step of using a first roller having a peripheral surface with an uneven shape and a second roller having a peripheral surface with an uneven shape that is to engage with the uneven shape of the first roller and allowing an engagement portion between the two rollers to bite the first nonwoven fabric to form unevenness on the first nonwoven fabric; and
a fusing and perforating step of, while the first nonwoven fabric with the formed unevenness is supported on the peripheral surface of the first roller, laminating the second nonwoven fabric on the first nonwoven fabric, fusing the second nonwoven fabric with the first nonwoven fabric at positions corresponding to projections of the first roller to form the fusion bond portions, and further forming the openings at forming positions of the fusion bond portions, wherein
the fusing and perforating step comprises bringing a tip of a projection of the first roller into contact with the first nonwoven fabric at a position where the opening is to be formed, and concurrently, allowing the projection to penetrate a melted part, so that a meltage of the fusion bond portion is unevenly distributed on a side of the second nonwoven fabric, thereby forming the protrusion.

<31> The method for manufacturing a three-dimensional perforated sheet as set forth in clause <30>, wherein an outlet wrap angle of the second nonwoven fabric to the first roller is preferably 5 degrees or more and more preferably 10 degrees or more.

<32> The method for manufacturing a three-dimensional perforated sheet as set forth in clause <30> or <31>, wherein an inlet wrap angle of the second nonwoven fabric to the first roller is preferably 5 degrees or more and more preferably 10 degrees or more.

<33> The method for manufacturing a three-dimensional perforated sheet as set forth in any one of clauses <30> to <32>, wherein the first roller has a radius of preferably 30 mm or more and more preferably 50 mm or more, and preferably 300 mm or less and more preferably 200 mm or less.

<34> The method for manufacturing a three-dimensional perforated sheet as set forth in any one of clauses <30> to <33>, wherein a conveyance speed of the second nonwoven fabric is increased or reduced relative to a rotation speed of the first roller.

<35> The method for manufacturing a three-dimensional perforated sheet as set forth in any one of clauses <30> to <34>, wherein the second nonwoven fabric to which tension is applied is fused with the first nonwoven fabric, and after a process with the first roller, the tension applied to the second nonwoven fabric is released.

INDUSTRIAL APPLICABILITY

According to the present invention, an absorbent article having excellent absorbability for both low viscosity excrements and high viscosity excrements is provided. According to the present invention, a three-dimensional perforated sheet suitable for a topsheet in a high-quality absorbent article having excellent permeability for both low viscosity excrements and high viscosity excrements can be efficiency produced.

The invention claimed is:
1. An absorbent article having a longitudinal direction coincident with a front-to-rear direction of a wearer and a lateral direction orthogonal to the longitudinal direction, the absorbent article comprising:
a topsheet;
a liquid-permeable sublayer; and
a liquid-retentive absorbent member,
the topsheet, the liquid-permeable sublayer, and the liquid-retentive absorbent member are configured to be sequentially stacked in increasing order of distance from a skin of a wearer, wherein the topsheet includes a laminate of a first nonwoven fabric and a second nonwoven fabric, the laminate has a plurality of openings penetrating the laminate in a thickness direction, the first nonwoven fabric and the second nonwoven fabric are fused together at peripheral edges of the openings to form a plurality of fusion bond portions, the first nonwoven fabric in a region other than the fusion bond portions protrudes in a direction away from the second nonwoven fabric configured to form a plurality of projections protruding toward a skin of a wearer, each fusion bond portion of the topsheet has a protrusion protruding toward the sublayer, and a plurality of the protrusions are dispersed on a surface of the topsheet facing the sublayer, and when the topsheet is pressed toward the sublayer, the sublayer is partially pressed by the protrusions of the topsheet, wherein in the sublayer, portions overlapping with the openings have a larger average distance between fibers than that of portions overlapping with the protrusions.

2. The absorbent article according to claim 1, wherein in a cross section of the topsheet in a certain direction in an in-plane direction, an outermost edge of the projection in the certain direction is located outward in the certain direction from the protrusion in vicinity of the projection.

3. The absorbent article according to claim 1, wherein in a cross section of the topsheet in the longitudinal direction, an outermost edge of the projection in the longitudinal direction is located outward in the longitudinal direction from the protrusion in vicinity of the projection.

4. The absorbent article according to claim 1, wherein in a cross section of the topsheet in any direction in an in-plane direction, an outermost edge of the projection in the any direction is located outward in the any direction from the protrusion in vicinity of the projection.

5. The absorbent article according to claim 1, wherein one of the openings is formed inside each of the plurality of fusion bond portions and penetrates the first nonwoven fabric and the second nonwoven fabric.

6. The absorbent article according to claim 5, wherein a shape of the opening in a plan view is a similar figure formed by uniformly reducing a shape of the fusion bond portion in a plan view.

7. The absorbent article according to claim 1, wherein the fusion bond portion has a film portion formed by making constituent fibers of the topsheet into a film.

8. The absorbent article according to claim 7, wherein a peripheral edge of the opening and a vicinity thereof are the film portion, and another region in the topsheet is not made into a film.

9. The absorbent article according to claim 7, wherein a tip of the protrusion in a protruding direction toward the sublayer is the film portion.

10. The absorbent article according to claim 1, wherein each of the first nonwoven fabric and the second nonwoven fabric includes an air-through nonwoven fabric or a spunbonded nonwoven fabric.

11. The absorbent article according to claim 1, wherein the sublayer is an air-through nonwoven fabric, a resin bonded nonwoven fabric, or an airlaid nonwoven fabric.

12. The absorbent article according to claim 1, wherein in the first nonwoven fabric, portions positioned among the plurality of fusion bond portions convexly project in a direction opposite to the second nonwoven fabric to form a plurality of hollow projections.

13. The absorbent article according to claim 1, wherein in the topsheet, a side on the second nonwoven fabric or a non-skin-facing surface side is substantially flat, and on a side on the first nonwoven fabric or on a skin-facing surface side, the projections, the openings, and the plurality of fusion bond portions constitute unevenness with large roughness.

14. The absorbent article according to claim 1, wherein the topsheet has, in a sheet plane thereof, a first direction and a second direction orthogonal thereto, in the absorbent article, the first direction is coincident with the longitudinal direction of the absorbent article, and the second direction is coincident with the lateral direction of the absorbent article, and the first direction of the topsheet is coincident with a main fiber orientation direction of constituent fibers of the first nonwoven fabric and the second nonwoven fabric.

15. The absorbent article according to claim 1, wherein the openings together with the plurality of fusion bond portions and the projections are alternately aligned in both the longitudinal direction and the lateral direction.

16. The absorbent article according to claim 1, wherein the openings together with the plurality of fusion bond portions are aligned in a direction inclined to the longitudinal direction and the lateral direction while spaced at regular intervals, and the projections are aligned in a direction inclined to the longitudinal direction and the lateral direction while spaced at regular intervals.

17. The absorbent article having a longitudinal direction coincident with a front-to-rear direction of a wearer and a lateral direction orthogonal to the longitudinal direction, the absorbent article comprising:

a topsheet;

a liquid-permeable sublayer; and a liquid-retentive absorbent member, the topsheet, the liquid-permeable sublayer, and the liquid-retentive absorbent member are configured to be sequentially stacked in increasing order of distance from a skin of a wearer, wherein the topsheet includes a laminate of a first nonwoven fabric and a second nonwoven fabric, the laminate has a plurality of openings penetrating the laminate in a thickness direction, the first nonwoven fabric and the second nonwoven fabric are fused together at peripheral edges of the openings to form a plurality of fusion bond portions, the first nonwoven fabric in a region other than the fusion bond portions protrudes in a direction away from the second nonwoven fabric configured to form a plurality of projections protruding toward a skin of a wearer, each fusion bond portion of the topsheet has a protrusion protruding toward the sublayer, and a plurality of the protrusions are dispersed on a surface of the topsheet facing the sublayer, and when the topsheet is pressed toward the sublayer, the sublayer is partially pressed by the protrusions of the topsheet, wherein a forming material of the protrusion is unevenly distributed at a part of the circumference of the opening.

18. The absorbent article having a longitudinal direction coincident with a front-to-rear direction of a wearer and a lateral direction orthogonal to the longitudinal direction, the absorbent article comprising:

a topsheet;

a liquid-permeable sublayer; and a liquid-retentive absorbent member, the topsheet, the liquid-permeable sublayer, and the liquid-retentive absorbent member are configured to be sequentially stacked in increasing order of distance from a skin of a wearer, wherein the topsheet includes a laminate of a first nonwoven fabric and a second nonwoven fabric, the laminate has a plurality of openings penetrating the laminate in a thickness direction, the first nonwoven fabric and the second nonwoven fabric are fused together at peripheral edges of the openings to form a plurality of fusion bond portions, the first nonwoven fabric in a region other than the fusion bond portions protrudes in a direction away from the second nonwoven fabric configured to form a plurality of projections protruding toward a skin of a wearer, each fusion bond portion of the topsheet has a protrusion protruding toward the sublayer, and a plurality of the protrusions are dispersed on a surface of the topsheet facing the sublayer, and when the topsheet is pressed toward the sublayer, the sublayer is partially pressed by the protrusions of the topsheet, wherein the forming material of the protrusion is unevenly distributed at both longitudinal sides of the opening, and the forming material is absent at both lateral sides of the opening, or an amount of the forming material of the opening is smaller at the both lateral sides than at the longitudinal sides.

19. The absorbent article having a longitudinal direction coincident with a front-to-rear direction of a wearer and a lateral direction orthogonal to the longitudinal direction, the absorbent article comprising:

a topsheet;

a liquid-permeable sublayer; and a liquid-retentive absorbent member, the topsheet, the liquid-permeable sublayer, and the liquid-retentive absorbent member are configured to be sequentially stacked in increasing order of distance from a skin of a wearer, wherein the topsheet includes a laminate of a first nonwoven fabric and a second nonwoven fabric, the laminate has a plurality of openings penetrating the laminate in a thickness direction, the first nonwoven fabric and the second nonwoven fabric are fused together at peripheral edges of the openings to form a plurality of fusion bond portions, the first nonwoven fabric in a region other than the fusion bond portions protrudes in a direction away from the second nonwoven fabric configured to form a plurality of projections protruding toward a skin of a wearer, each fusion bond portion of the topsheet has a protrusion protruding toward the sublayer, and a plurality of the protrusions are dispersed on a surface of the topsheet facing the sublayer, and when the topsheet is pressed toward the sublayer, the sublayer is partially pressed by the protrusions of the topsheet, wherein in a condition in which a body pressure of a wearer is applied to the topsheet, high fiber density portions having a relatively high fiber density are formed in the sublayer in regions corresponding to the protrusions, concurrently low fiber density portions having a relatively low fiber density are formed in other regions of the sublayer, and the low fiber density portions overlap with forming positions of the projections.

* * * * *